United States Patent [19]

Courteille et al.

[11] Patent Number: 5,665,384

[45] Date of Patent: Sep. 9, 1997

[54] OILY CAPSULES OF KETOPROFEN

[75] Inventors: Frederic Courteille, Cachan; Michel Veillard, Sceaux, both of France

[73] Assignee: Rhone-Poulenc Rorer S.A., Antony Cedex, France

[21] Appl. No.: 258,905

[22] Filed: Jun. 13, 1994

Related U.S. Application Data

[63] Continuation of Ser. No. 934,531, filed as PCT/FR91/00273, Apr. 4, 1991, abandoned.

[30] Foreign Application Priority Data

Apr. 6, 1990 [FR] France ................. 9004468

[51] Int. Cl.⁶ .................. A61K 35/37; A61K 35/38
[52] U.S. Cl. .................. 424/451; 424/455; 424/456; 424/452
[58] Field of Search .................. 424/451, 455, 424/456, 452

[56] References Cited

U.S. PATENT DOCUMENTS 4,627,850  12/1986  Deters et al. ................ 424/452
4,944,949   7/1990  Story et al. ................. 424/456

Primary Examiner—Thurman K. Page
Assistant Examiner—William E. Benston, Jr.
Attorney, Agent, or Firm—Ross J. Oehler

[57] ABSTRACT

Stable, pharmaceutical ketoprofen salts for oral administration are provided in oily solutions to avoid direct contact of acid forms of ketoprofen with the gastric or duodenal mucus membranes. Sodium, arginine, lysine and/or N-methylglucamine salts of ketoprofen are disclosed in solutions of polyoxyethyenatide vegetable oil, castor oil, esters of fatty acids and/or polyols. These oily solutions of ketoprofen may be administered orally in capsule form.

11 Claims, No Drawings

OILY CAPSULES OF KETOPROFEN

This is a continuation of application Ser. No. 07/934,531, filed as PCT/FR91/00273, Apr. 4, 991, abandoned.

The present invention relates to a novel pharmaceutical form of ketoprofen. It relates more particularly to a capsule containing ketoprofen in oily solution.

Ketoprofen or 2-(3-benzoylphenyl)propionic acid has been marketed for a long time in the form of tablets with immediate action or with prolonged action and in injectable form, either ready to use, or lyophilised. When it is marketed in the form of tablets the acid form of ketoprofen is used, when it is marketed in injectable form either its sodium salt or a nitrogenous salt such as the arginine and/or lysine and/or N-methylglucamine salt is used.

When it is used in its acid form, hence orally, ketoprofen has a tendency during its absorption to provoke gastric or duodenal irritation by contact of the crystals of active principle with the mucous membranes, which results in a very high local concentration of active principle.

When the pharmaceutical industry sought to prepare forms intended for oral absorption starting from one of the salts of ketoprofen, great difficulties of stability of tablets thus prepared became evident because the salts of ketoprofen have such a hygroscopicity that the tablet has a tendency to degrade rapidly or it is necessary to keep the latter in packaging having a strictly controlled atmosphere as far as hygrometry is concerned.

The injectable forms do not have this disadvantage because either they are presented in hermetic bottles or they are in aqueous solution and hence do not have problems associated with hygrometry phenomena.

In order to avoid direct contact of the gastric or duodenal mucous membrane with the acidic form of ketoprofen, an oral form of administration of ketoprofen in salt form has been sought for a long time.

The present invention has allowed this objective to be achieved.

It relates to capsules containing an oily solution of ketoprofen.

This solution is obtained by dissolving a salt of ketoprofen chosen from amongst the sodium, arginine and/or lysine and/or N-methylglucamine salt in a polyoxyethylenated vegetable oil, an ester of a fatty acid and of an alcohol or of a polyol or castor oil. Among the polyoxyethylenated vegetable oils, the oils sold by GATTEFOSSE under the trade name LABRAFIL can be cited.

After numerous attempts to solubilise the sodium salt in different oily compositions, it became evident that the polyoxyethylenated vegetable oil sold under the name LABRAFIL allowed the best economy, tolerance and solubility relation for ketoprofen.

It became evident that the polyoxyethylenated oils had still further improved solubility properties if they were combined with one or more third substances such as, for example: polyethylene glycol 400, ethyl oleate, Cremophor EL, ethanol, emulsifying agents such as esters of sorbitan and polyoxyethylene (Tween 80), neutral oil composed of saturated fatty acid triglycerides of medium chain length (8 to 10 carbon atoms) (Miglyol 812) and corn oil.

It is preferred from amongst all these combinations to use the polyoxyethylenated oils combined with polyethylene glycol 400 or with a mixture of ethanol and of polysorbate 80 (Tween 80). It must be specified that in all these combinations at least 90% of oil is used.

The preferred pharmaceutical compositions according to the invention contain between:
1 to 8% by weight of ketoprofen sodium
94 to 77% by weight of Labrafil M.1944
5 to 15% by weight of 95 ethanol or of a 50/50 mixture of ethanol and of polysorbate 80 (Tween 80).

This solution is prepared by mixing of the components of the excipient, followed by a slow incorporation of ketoprofen sodium and stirring until complete dissolution of the ketoprofen sodium. The division and distribution is carried out in capsules, which are sealed by any appropriate technique such as, for example, by means of a banderole of gelatin (Eli Lilly technique) or pulverisation and drying of a mixture of water and of alcohol (Capsugel technique).

The present invention will be more completely described with the aid of the following examples which must not be considered as limiting the invention.

EXAMPLE 1

With protection from light, LABRAFIL M.1944 CS (3749.85 g) is mixed with 95° ethanol (450 g). In an attached container, with stirring, sodium ketoprofenate (300.15 g) is incorporated in approximately 30% of the above mixture. The remainder of the excipient is then poured in and stirring of the mixture is continued until complete dissolution of the ketoprofen (about 5 hours). The final weight of the preparation is adjusted to compensate for the losses of ethanol. The mixture is filtered on a Millipore filter of 10 _m porosity.

The division into capsules is carried out with the aid of a HOFLIGER and KARG GKF 400L machine, at a rate of 0.43 ml of solution per capsule for a No. 3 capsule. Approximately 9000 capsules are obtained. The full capsules are sealed with a banderole of gelatin with the aid of a Qualiseal machine under a pressure of 200 mPas. The capsules are then dried with protection from light.

After analysis, a content of ketoprofen per capsule of 24.5 mg is obtained for a theoretical content of 25 mg of ketoprofen acid.

EXAMPLE 2

Example 1 is reproduced using 95° ethanol (225 g) and polysorbate 80 (225 g) as excipient in place of the ethanol (450 g). The preparation of the solution and distribution into capsules are carried out as in the preceding example.

After analysis, a content of ketoprofen per capsule of 24.8 mg is obtained for a theoretical content of 25 mg of ketoprofen base acid.

EXAMPLES 3 AND 4

Examples 1 and 2 are reproduced using sodium ketoprofenate (600.30 g) which is dissolved in, respectively, LABRAFIL (7500 g) with ethanol (900 g) or ethanol (450 g) and polysorbate 80 (450 g) which is distributed into No. 0 capsules (1 ml).

Capsules containing the equivalent of 50 mg of ketoprofen acid are obtained.

We claim:

1. A pharmaceutical composition comprising an oil solution of a ketoprofen salt, wherein oil is present in an amount greater than about 90% by weight of the solution and wherein ketoprofen salt is present in an amount of 1–8% by weight of the solution.

2. The composition according to claim 1, wherein the salt is selected from the group consisting of sodium salt, arginine salt lysine salt and N-methylglucamine salt of ketoprofen.

3. The composition according to claim 1, which contains a concentration by weight of ketoprofen salt of 5% expressed as ketoprofen acid.

4. The composition according to claim 1, wherein the oil solution comprises polyoxyethylenated vegetable oil, castor oil, esters of fatty acids, and polyols.

5. A pharmaceutical composition for oral administration comprising an oil solution of a ketoprofen salt and a ketroprofen salt solubility enhancer.

6. The pharmaceutical composition according to claim 5, wherein the salt is selected from the group consisting of sodium salt, arginine salt, lysine salt and N-methylglucamine salt of ketoprofen.

7. The pharmaceutical composition according to claim 5, wherein the oil comprises polyoxyethylenated vegetable oil, castor oil, esters of fatty acids, and polyols.

8. The pharmaceutical composition according to claim 5, wherein the ketoprofen salt solubility enhancer is selected from the group consisting of polyethylene glycol, ethyl oleate, Cremophor EL, ethanol, esters of sorbitan and polyoxyethylene.

9. The pharmaceutical composition according to claim 8, wherein the ketoprofen salt solubility enhancer is ethanol.

10. The pharmaceutical composition according to claim 8, wherein the ketoprofen salt solubility enhancer is an ester of sorbitan.

11. The pharmaceutical composition according to claim 8, wherein the ketoprofen salt solubility enhancer is an ester of polyoxyethylene.

* * * * *